(12) United States Patent
Forstein et al.

(10) Patent No.: US 11,291,512 B2
(45) Date of Patent: Apr. 5, 2022

(54) ROBOT SPECIFIC IMPLANT DESIGNS WITH CONTINGENT MANUAL INSTRUMENTATION

(71) Applicant: THINK SURGICAL, INC., Fremont, CA (US)

(72) Inventors: Micah Forstein, Fremont, CA (US); Kyle Kuznik, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 0 days.

(21) Appl. No.: 16/875,173

(22) Filed: May 15, 2020

(65) Prior Publication Data

US 2020/0367980 A1 Nov. 26, 2020

Related U.S. Application Data

(60) Provisional application No. 62/850,365, filed on May 20, 2019.

(51) Int. Cl.
| | |
|---|---|
| *A61B 17/00* | (2006.01) |
| *A61B 34/30* | (2016.01) |
| *A61B 17/15* | (2006.01) |
| *A61F 2/46* | (2006.01) |
| *A61B 34/10* | (2016.01) |
| *A61B 34/00* | (2016.01) |

(52) U.S. Cl.
CPC ............ *A61B 34/30* (2016.02); *A61B 17/155* (2013.01); *A61F 2/461* (2013.01); *A61B 2017/00973* (2013.01); *A61B 2034/105* (2016.02); *A61B 2034/742* (2016.02); *A61B 2034/743* (2016.02); *A61B 2034/744* (2016.02)

(58) Field of Classification Search
CPC combination set(s) only.
See application file for complete search history.

(56) References Cited

U.S. PATENT DOCUMENTS

| | | | |
|---|---|---|---|
| 5,755,803 A | 5/1998 | Haines et al. | |
| 2013/0211531 A1 | 8/2013 | Steines et al. | |
| 2015/0182343 A1 | 7/2015 | Nadzadi et al. | |
| 2016/0045268 A1 | 2/2016 | Keppler et al. | |
| 2018/0338839 A1* | 11/2018 | Ferko ................... | A61B 5/4528 |

FOREIGN PATENT DOCUMENTS

WO 2011028624 A1 3/2011

\* cited by examiner

*Primary Examiner* — Sameh R Boles
(74) *Attorney, Agent, or Firm* — Blue Filament Law PLLC

(57) ABSTRACT

A system and method are described herein for creating planar bone cuts on a bone to receive a total knee arthroplasty (TKA) femoral implant. The system includes a robotic surgical device, a computing system, and one or more contingent manual instruments. A surgical plan is generated having instructions for the robotic surgical device to create six or more planar bone cuts on the bone. The robotic surgical device executes the instructions, and in the event the robotic procedure is aborted before completing the six or more planar cuts, the one or more contingent manual instruments are used to create any remaining planar bone cuts. The one or more contingent manual instruments may include a plurality of uniquely arranged guide slots to assist a user in creating one or more remaining planar bone cuts.

11 Claims, 6 Drawing Sheets

ROBOT SPECIFIC IMPLANT DESIGNS WITH CONTINGENT MANUAL INSTRUMENTATION

RELATED APPLICATIONS

This application claims priority benefit of U.S. Provisional Application Ser. No. 62/850,365 filed 20 May 2019, the contents of which are hereby incorporated by reference.

TECHNICAL FIELD

The present invention generally relates to the field of robotic orthopedic surgery, and more particularly to robot specific implant designs that exploit a robot's ability to create precise bone cuts. The present invention further provides one or more contingent manual instruments to complete the bone cuts.

BACKGROUND

Total knee arthroplasty (TKA) is a surgical procedure in which the articulating surfaces of the knee joint are replaced with prosthetic components, or implants. TKA requires the removal of worn or damaged articular cartilage and bone on the distal femur and proximal tibia. The removed cartilage and bone are then replaced with synthetic implants, typically formed of metal or plastic, to create new joint surfaces. The position and orientation (POSE) of the removed bone, referred to as bone cuts or reselected bone, determines the final placement of the implants within the joint. Generally, surgeons plan and create the bone cuts so the final placement of the implants restores the mechanical axis or kinematics of the patient's leg while preserving the balance of the surrounding knee ligaments. Even small implant alignment errors outside of clinically acceptable ranges correlate with worse outcomes and increased rates of revision surgery.

Current TKA femoral implants are designed to be installed using specific manual instrumentation (e.g., cutting guides, cutting blocks, alignment fixtures). Due to the requirements of the manual instrumentation and complexity of the procedure, the number of bone cuts to create the new joint surfaces is limited and can remove more bone than is needed to secure the implant to the bone. Most commonly, the number of bone cuts is limited to five planar cuts. FIG. 1 illustrates a patient's distal femur 10 and a contour matching femoral prosthesis 12 for a TKA procedure, where the five femoral cut planes include the anterior cut plane 14, anterior chamfer cut plane 16, the distal cut plane 18, the posterior chamfer cut plane 20, and the posterior cut plane 22. It should be appreciated that the resulting five mating planes of the current implant designs compromise the bone through increased bone removal in order to reduce to the complexity of the surface preparation with these manual instruments.

Robotic surgery can overcome these limitations of the manual instruments. While a human can control a tool with unidirectional precision, a computer controlled robot can operate in a controlled manner in two or more degrees of freedom, and six degree of freedom controlled movement is routine now for robots. As a result, the robot can be controlled in several degrees of freedom to create planar, as well as non-planar bone cuts. The resolution of the bone cuts are also improved well beyond what a surgeon can do with manual instruments. However, the vast majority of implants are still designed and manufactured to accommodate manual bone preparation. As robotic-assisted surgery becomes more mainstream, there is an opportunity to improve the implant designs to exploit the robot's ability to create more precise and intricate bone cuts. These implant designs are referred to herein as robot specific implant designs.

With any robot specific implant design, there needs to be a contingency in the event the robotic surface preparation is aborted. A robotic surgical procedure may be aborted for a variety of reasons including hardware/software faults, unexpected bone geometries, poor bone quality, unexpected boney or soft tissue features, and/or at the discretion of the surgeon. In the event the procedure is aborted, the surgeon will need to complete the surgery manually for the robot specific implant designs.

Thus, there exists a need for a system and method to improve the design of an implant to exploit a robot's ability to create precise bone cuts. There is a further need for a system and method to create the bone cuts for the robot specific implant designs. There is an even further need to provide manual instrumentation for the robot specific implant designs.

SUMMARY

A method for creating planar bone cuts on a bone to receive a total knee arthroplasty (TKA) femoral implant is described herein. A surgical plan is generated having instructions for a robotic surgical device to create six or more planar bone cuts on the bone. The instructions are executed with the robotic surgical device. The execution of the instructions is aborted before the completion of the six or more planar cuts and the remaining planar cuts are created using manual instruments. After the six or more planar cuts are created, a TKA implant having six or more planar mating surfaces may be installed on the bone.

A method to design an implant and execute a robotic surgical procedure is described herein. Pre-operative bone data of a bone is provided to a computer having a pre-operative planning software program. A position for an implant having six or more planar surfaces is planned relative to the pre-operative bone data. A set of instructions is generated for a robotic surgical device to create six or more corresponding planar bone cuts to mate with complementary planar surfaces of the implant. The set of instructions are then executed with the robotic surgical device.

A surgical system is described herein. The surgical system includes a robotic arm, a computing system, and one or more contingent manual instruments. The robotic arm controls an end-effector. The computing system has one or more processors and memory. The memory stores a surgical plan having instructions for the robotic arm to actuate the end-effector to create six or more planar bone cuts on a bone. The one or more processors executes the instructions to control the robotic arm to create the six or more planar bone cuts with the end-effector. The one or more contingent manual instruments, each alone or in combination, create any remaining planar bone cuts in the event the execution of the instructions is aborted prior to the completion of the six or more planar bone cuts.

BRIEF DESCRIPTION OF THE DRAWINGS

The present invention is further detailed with respect to the following drawings that are intended to show certain aspects of the present of invention, but should not be construed as limit on the practice of the invention, wherein:

FIG. 2A is a perspective view thereof, and FIG. 2B is a side view thereof;

FIG. 3A is a top perspective view of a first cut block, FIG. 3B is a bottom perspective view of the first cut block, and FIG. 3C is top perspective view of an embodiment of a second cut block;

DETAILED DESCRIPTION

Figure 1:
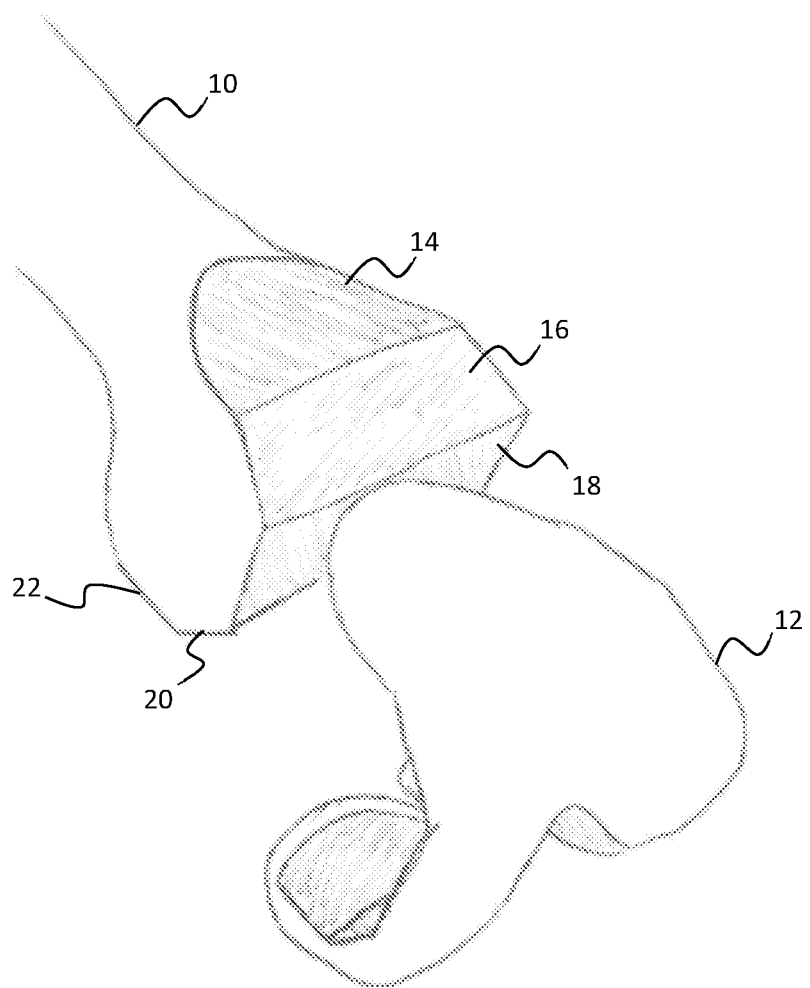
FIG. 1 depicts a prepared bone to receive a prior-art femoral TKA implant.

The present invention has utility as a system and method to improve the design of an implant to exploit a robot's ability to create more precise and intricate bone cuts. The improved robotic implant designs confer a better fit and alignment on the bone, while preserving additional bone when compared to manual procedures. Further, the present invention provides the user with fallback manual instrumentation in the event the robotic procedure needs to be aborted. The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular inventive embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

Further, it should be appreciated that although the systems and methods described herein make reference to total knee arthroplasty, the systems and methods may be applied to other robotic-assisted surgical procedures involving other bones and joints in the body illustratively including the hip, ankle, elbow, wrist, skull, and spine, as well as revision of initial repair or replacement of any of the aforementioned bones or joints.

All publications, patent applications, patents and other references mentioned herein are incorporated by reference in their entirety.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein, the term "digitizer" refers to a device capable of measuring, collecting, designating, or recording the position of physical coordinates in three-dimensional space. For example, the 'digitizer' may be: a "mechanical digitizer" having passive links and joints, such as the high-resolution electro-mechanical sensor arm described in U.S. Pat. No. 6,033,415; a non-mechanically tracked digitizer probe (e.g., optically tracked, electromagnetically tracked, acoustically tracked, and equivalents thereof) as described in, for example, U.S. Pat. No. 7,043,961; a digitizer probe as described in U.S. Pat. No. 8,615,286; or an end-effector of a robotic device.

As used herein, the term "digitizing" refers to the collecting, measuring, designating, and/or recording of physical points in space with a digitizer.

As used herein, the term "pre-operative bone data" refers to bone data used to pre-operatively plan a procedure before making modifications to the actual bone. The pre-operative bone data may include one or more of the following. An image data set of a bone (e.g., computed tomography, magnetic resonance imaging, ultrasound, x-ray, laser scan), a virtual generic bone model, a physical bone model, a virtual patient-specific bone model generated from an image data set of a bone, or a set of data collected directly on a bone intra-operatively commonly used with imageless computer-assist devices.

As used herein, the term "registration" refers to the determination of the POSE and/or coordinate transformation between two or more objects or coordinate systems such as a computer-assist device, a bone, pre-operative bone data, surgical planning data (i.e., an implant model, cut-file, virtual boundaries, virtual planes, cutting parameters associated with or defined relative to the pre-operative bone data), and any external landmarks (e.g., a tracking marker array) associated with the bone, if such landmarks exist. Methods of registration known in the art are described in U.S. Pat. Nos. 6,033,415; 8,010,177; and 8,287,522.

Also, referenced herein is a surgical plan. For context, the surgical plan is created, either pre-operatively or intra-operatively, by a user using planning software. The planning software may be used to plan the position for an implant relative to pre-operative bone data. For example, the planning software may be used to generate three-dimensional (3-D) models of the patient's bony anatomy from a computed tomography (CT), magnetic resonance imaging (MRI), x-ray, ultrasound image data set, or from a set of points collected on the bone intra-operatively. A set of 3-D computer aided design (CAD) models of the manufacturer's prosthesis are pre-loaded in the software that allows the user to place the components of a desired prosthesis to the 3-D model of the boney anatomy to designate the best fit, position, and orientation of the implant to the bone. The planning software may additionally or alternatively include tools to custom design an implant relative to boney features.

As used herein, the term "real-time" refers to the processing of input data within milliseconds such that calculated values are available within 10 seconds of computational initiation.

Also described herein are "robotic surgical systems". A robotic surgical system refers to a system (or device) requiring computer control of an end-effector to aid in a surgical procedure. Examples of a robotic surgical systems include active and haptic, 1 to N degree(s) of freedom (DOF) hand-held surgical devices and systems, autonomous serial-chain manipulator systems, haptic serial chain manipulator systems, parallel robotic systems, master-slave robotic systems, etc., as described in, for example, U.S. Pat. Nos. 5,086,401; 7,206,626; 8,876,830; 8,961,536; and 9,707,043; and U.S. Pat. App. Pub. US20180344409A1, which patents, patent publications and patent applications are hereby incorporated herein by reference. A particular embodiment of a robotic surgical system as described in detail below.

Figure 2A:
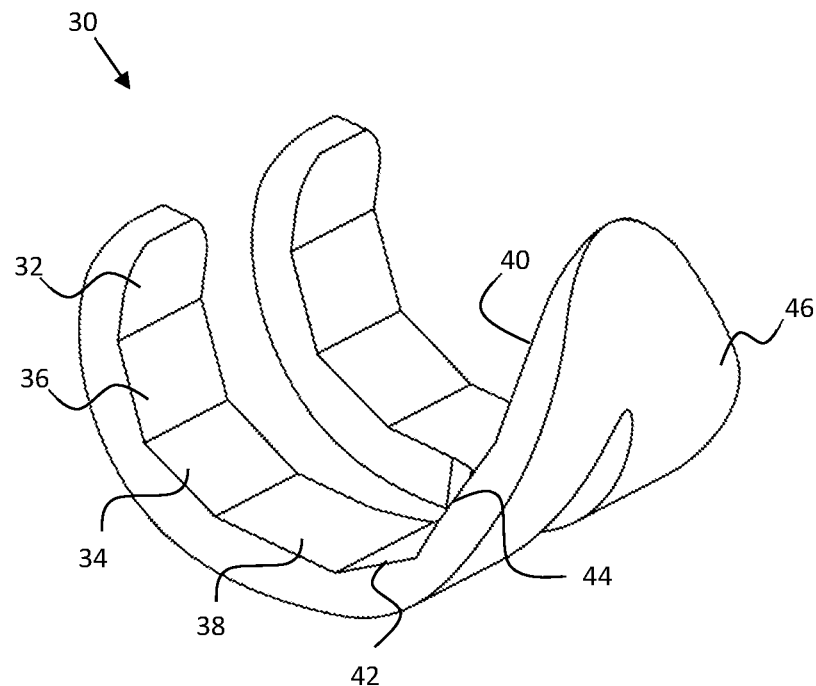
FIGS. 2A and 2B depict a robot-specific femoral TKA implant having seven planar bone-contacting surfaces in accordance with embodiments of the invention, where
Figure 2B:
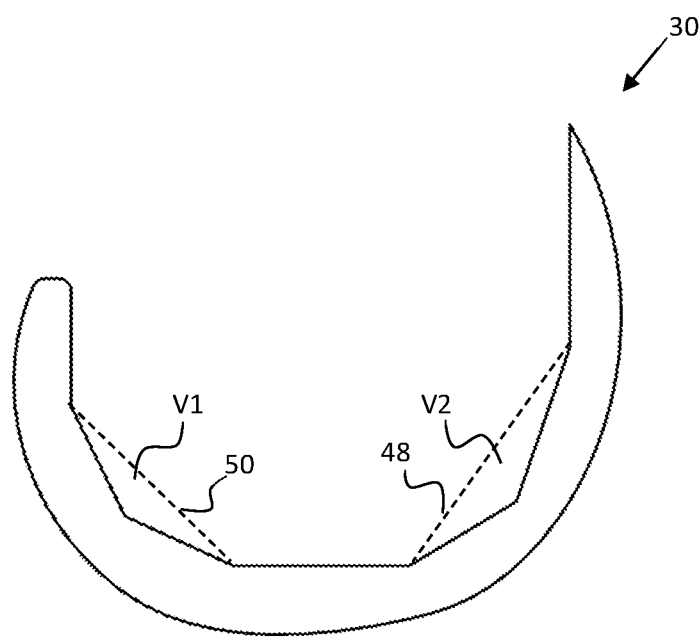

Embodiments of the invention provide robot-specific femoral total knee arthroplasty (TKA) implants that exploit a robot's ability to create more precise and intricate bone cuts. The robot-specific femoral TKA implants have six or more planar bone-contacting surfaces to increase the contact surface area with the bone and to preserve additional bone when compared to femoral implants with five or less planar surfaces. Referring now to the figures, FIGS. 2A and 2B illustrate a robot-specific femoral TKA implant 30 having seven bone-contacting planar surfaces. The femoral TKA implant 30 includes a posterior plane 32, a first posterior chamfer plane 34, a second posterior chamfer plane 36, a distal plane 38, an anterior plane 40, a first anterior chamfer plane 42, and a second anterior chamfer plane 44. Opposing the seven bone-contacting planar surfaces is the femoral articulating surface 46 that mates with and articulates against a tibial TKA implant, and may particularly articulate against a liner/spacer associated with the tibial TKA implant. Having a femoral TKA implant with six or more planar bone-contacting surfaces preserves more of the native bone in TKA procedure and increases the contact surface area between the implant and the bone for additional stability. FIG. 2B depicts this bone conservation between an implant having seven planar surfaces compared to an implant having five planar surfaces. The dotted lines represent the anterior chamfer plane 48 and posterior chamfer plane 50 of a conventional implant having five planar surfaces with respect to the robot-specific femoral TKA implant 30 having seven planar surfaces. The volumes, V1 and V2, represent the additional volume of bone to be removed to receive a conventional implant compared to the robot-specific femoral TKA implant 30. While, FIGS. 2A and 2B depict an implant with seven bone-contacting planar surfaces, it is appreciated that variants thereof, with six, eight, nine, or even ten+ bone-contacting surfaces are provided within the spirit and scope of the present invention; these are intended to be incorporated within the scope of the present invention. Furthermore, whiles FIGS. 2A and 2B depict all seven bone-contacting planes having edges that are parallel, it should be appreciated that some of the planes need not have parallel edges and as a result, define facets with edge intersections that are, for example orthogonal to a contiguous plane.

Given the additional planar surfaces of the robot-specific femoral TKA implant 30, the bone is preferably prepared with a robotic surgical device. As the number of planar surfaces on the implant increases, the required resolution and precision to prepare the bone also increases. The robotic surgical device may prepare the bone by executing a set of instructions, where the set of instructions are based on at least one of: a geometry of the robot-specific femoral TKA implant (e.g., the boundaries of the implant, and/or the location of the planar surface); a geometry of the bone (e.g., the bone boundaries, a known volume of bone to be removed based on the geometry of the implant); a planned position of the robot specific femoral TKA implant relative to the femur (e.g., the intersecting lines or points between the implant with the bone); or a combination thereof. A user may plan the position of the implant relative to the bone in a pre-operative planning software program. The surgical plan may be generated by positioning a CAD model of the robot-specific femoral TKA implants relative to pre-operative bone data of the femur. The pre-operative planning program may further allow a user to custom design a robot-specific femoral TKA implant relative to the femur. The final surgical plan may include the set of instructions and the planned position of the implant relative to the femur to permit the robotic surgical device to execute the set of instructions on the femur in the planned location. In the operating room (OR), the bone is exposed and the surgical plan is registered with respect to the position of the bone in the coordinate system of the robotic surgical device. The set of instructions are then executed by the robotic surgical device to prepare the bone. After the bone is prepared, the robotic-specific femoral TKA implant is installed on the bone and the procedure is completed.

In certain circumstances, the robotic surgical procedure may need to be aborted before all of the planar surfaces are prepared on the bone. A robotic surgical procedure may be aborted for a variety of reasons including hardware/software faults, unexpected bone geometries, poor bone quality, unexpected boney or soft tissue features, and/or at the discretion of the surgeon. In the event the procedure is aborted, the surgeon needs to finish preparing the bone using manual instruments. In particular inventive embodiments, the manual instrumentation may include a set of cut blocks. Each version of the cut block includes a plurality of guide slots to guide a surgical saw to create the cut planes on the bone, where the angle and positioning of one or more of the guide slots on each cut block is different to create the different cut planes. For example, a first cut block may have guide slots positioned and angled to aid in creating the cut planes that contact the first anterior chamfer plane 42 and the first posterior chamfer plane 34 of the robot-specific femoral TKA implant 30. A second cut block may have guide slots positioned and angled to aid in creating the cut planes that contact the second anterior chamfer plane 44 and the second posterior chamfer plane 36 of the robot-specific femoral TKA implant 30. Additional versions of the cut blocks may be used to aid in the creation of additional cut planes (e.g., a third cut block to aid in the creation of two additional planes to receive a femoral TKA implant having 9 planes).

Figure 3A:
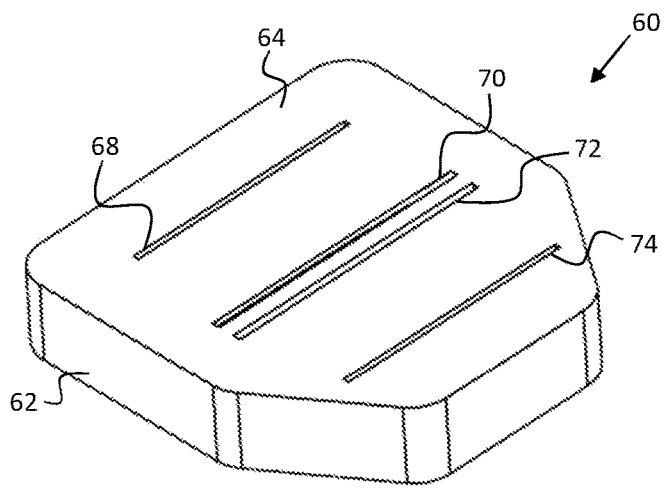
FIGS. 3A to 3C depict cut blocks to manually prepare the bone for a robot-specific femoral TKA implant in the event of an aborted robotic procedure in accordance with embodiments of the invention, where
Figure 3B:
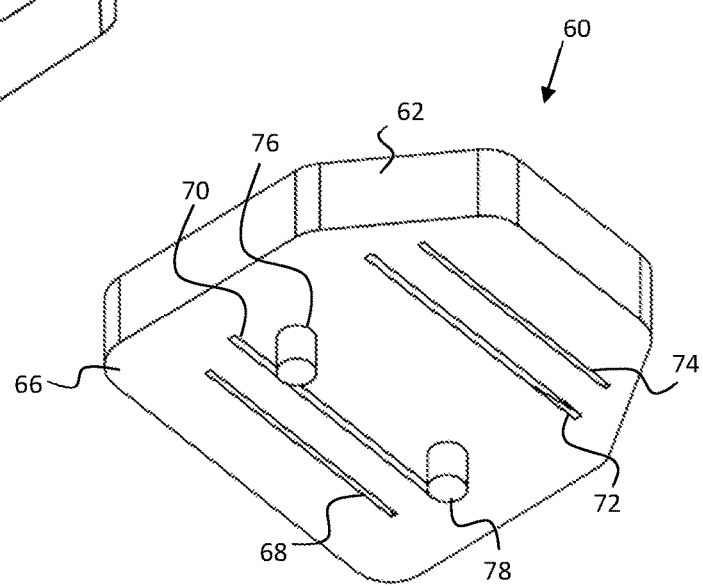
Figure 3C:
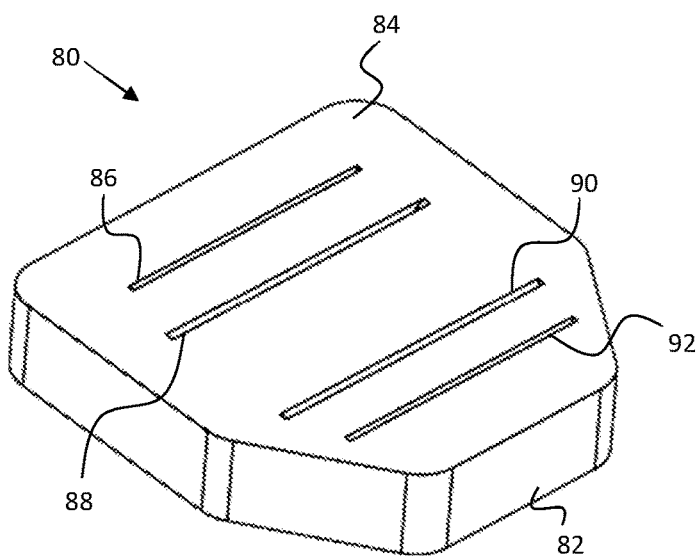
Figure 5:
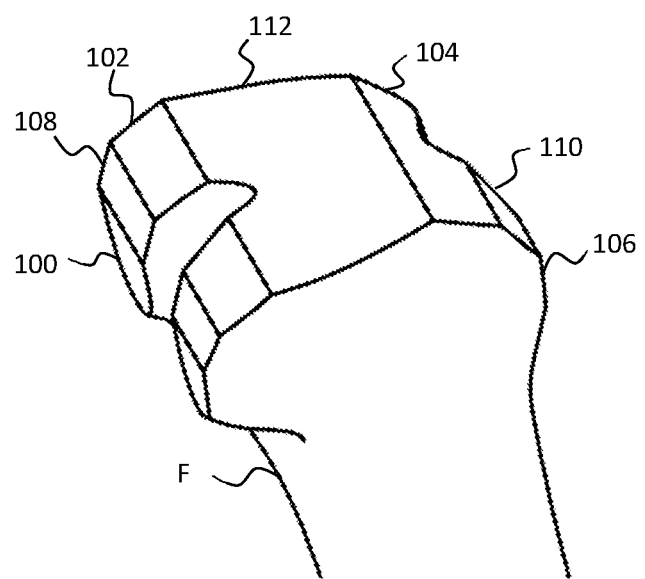
FIG. 5 depicts a prepared bone to receive a robot-specific femoral TKA implant in accordance with embodiments of the invention.

FIGS. 3A to 3C illustrate an example of a first cut block 60 and a second cut block 80 to manually prepare the bone for a robot-specific TKA implant in the event of an aborted robotic TKA procedure, where FIG. 3A depicts a top perspective view of a first cut block 60, FIG. 3B depicts a bottom perspective view of the first cut block 60, and FIG. 3C depicts a top perspective view of a second cut block 80. The first cut block 60 is a body 62 having a top surface 64, and a bottom surface 66 that contacts and lies against the distal cut plane on the femur. The first cut block 60 further includes a plurality of guide slots extending through the body 62 from the top surface 64 to the bottom surface 66. The first cut block 60 in some inventive embodiments includes a posterior guide slot 68, a first posterior chamfer guide slot 70, a first anterior chamfer guide slot 72, and an anterior guide slot 74. The first cut block 60 in some inventive embodiments further includes a pair of pegs (76 and 78) projecting from the bottom surface 66 where the pair of pegs (76 and 78) fit into corresponding peg holes made on the distal cut plane. The position of the pegs (76 and 78) on the cut block 60 are at a known geometry relative to the guide slots such that when the cut block 60 is assembled into the peg holes made on the distal cut plane, the guide slots are aligned to aid in the creation of the planned cut planes. The posterior guide slot 68 and the anterior guide slot 74 are configured to guide a surgical saw to create the posterior cut plane 100 (as shown in FIG. 5) and the anterior cut plane 106 (as shown in FIG. 5), respectively. The first posterior chamfer guide slot 70 and the first anterior chamfer guide slot 72 are angled and positioned to guide a surgical saw to create the first posterior chamfer cut plane 102 (as shown in FIG. 5) and the first anterior chamfer cut plane 104 (as shown in FIG. 5), respectively.

FIG. 3C illustrates a second cut block 80. The second cut block 80 is a body 82 having a top surface 84, and a bottom surface 85 (as shown in FIG. 4B) that contacts and lies against the distal cut plane on the femur in the same location as the first cut block 60. The second cut block 80 further includes a plurality of guide slots extending through the body 82 from the top surface 84 to the bottom surface 85. The second cut block 80 in some inventive embodiments includes a posterior guide slot 86, a second posterior chamfer guide slot 88, a second anterior chamfer guide slot 90, and an anterior guide slot 92. The second cut block 80 in some inventive embodiments further includes a pair of pegs (now shown) projecting from the bottom surface 85 similar to the pegs (76 and 78) described above. The position of the pair of pegs on the bottom surface 85 are known relative to the guide slots such that the guide slots align in the planned position when the pegs are inserted into the peg holes. The posterior guide slot 86 and the anterior guide slot 92 are configured to guide a surgical saw to create the posterior cut plane 100 (as shown in FIG. 5) and the anterior cut plane 106 (as shown in FIG. 4), respectively. The second posterior chamfer guide slot 88 and the first anterior chamfer guide slot 90 are angled and positioned to guide a surgical saw to create the second posterior chamfer cut plane 108 (as shown in FIG. 5) and the second anterior chamfer cut plane 110 (as shown in FIG. 5), respectively.

Figure 4A:
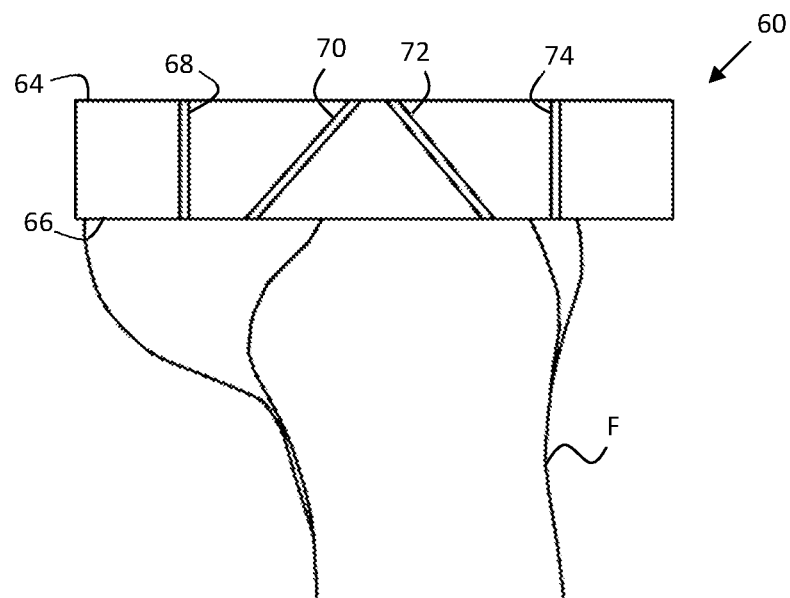
FIGS. 4A and 4B depict cross-sectional views of the first cut block (FIG. 4A) and second cut block (FIG. 4B) of FIGS. 3A to 3C on a distal cut plane of a femur in accordance with embodiments of the invention.
Figure 4B:
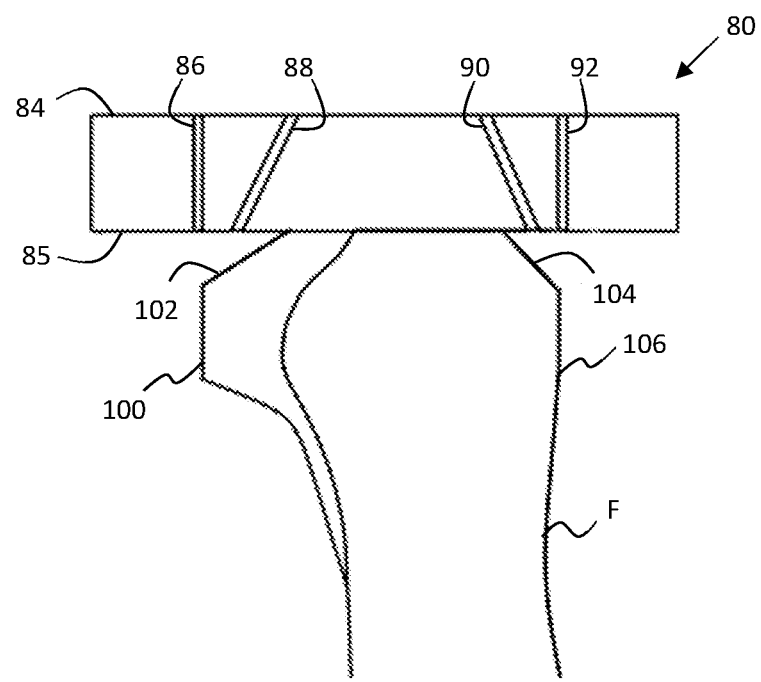

FIGS. 4A and 4B depicts an example of the first cut block 60 and the second cut block 80 in use, where FIG. 4A is a cross-sectional view of the first cut block 60 on the distal cut plane of a femur F, and FIG. 4B is a cross-sectional view of the second cut block 80 on the distal cut plane of the femur F. In this example, the robotic surgical device was able to prepare the distal cut plane and the peg holes that receive the pegs of the cut blocks before the robotic procedure was aborted. In particular inventive embodiments, the set of instructions for the robotic surgical device are configured to have the robotic device create the distal cut plane and the peg holes first, prior to creating any of the other cuts. This acts as a contingency plan to permit the use of the cut blocks in the event of an abortion of the robotic procedure any time after the distal cut plane and peg holes are created. The first cut block 60 is then assembled onto the distal cut plane by placing the pair of pegs (76 and 78) into the peg holes. The surgeon can then create the posterior cut plane 100, the first posterior chamfer cut plane 102, the first anterior chamfer cut plane 104, and the anterior cut plane 106 as shown in FIG. 4B. Subsequently, the first cut block 60 is removed from the femur F, and the second cut block 80 is assembled to the distal cut plane by placing the pair of pegs into the peg holes. The surgeon may then create the second posterior chamfer cut plane 108 and the second anterior chamfer cut plane 110. FIG. 5 illustrates the fully prepared bone to receive the robot-specific femoral TKA implant 30. Once prepared, the surgeon installs the robot-specific femoral TKA implant 30 on the bone and the procedure is completed.

It should be appreciated that various designs and/or configurations of one or more cut blocks may exist to finish preparing the bone. In a particular inventive embodiment, there is a single cut block having all the guide slots necessary to finish preparing the bone. This single cut block may illustratively include a posterior guide slot, a first posterior chamfer guide slot, a second posterior chamfer guide slot, an anterior guide slot, a first anterior chamfer guide slot, and a second anterior chamfer guide slot. Additional guide slots may be added depending on the number of planar surfaces of a robot-specific femoral TKA implant. In another inventive embodiment, a set of cut blocks are used as described above, but one or more guide slots from one guide block may be absent from another guide block. For example, the aforementioned second cut block 80 may not have the posterior guide slot 86 and anterior guide slot 92 because the first cut block 60 was able to aid in the creation of those cut planes.

It is further contemplated that other contingent manual instrumentation may be used in the event of an aborted robotic procedure. In a specific inventive embodiment, the manual instrumentation may include one or more 3-D printed cut guides. The 3-D printed cut guides may have one or more guide slots to guide a surgical saw in creating the cut planes. The 3-D printed cut guides further have a mating surface that is a negative match of a portion of the bone. The mating surface ensures the 3-D printed cut guide assembles to the bone in a desired position and orientation such that the guide slots are aligned in the planned location.

Robotic Surgical Device

Figure 6:
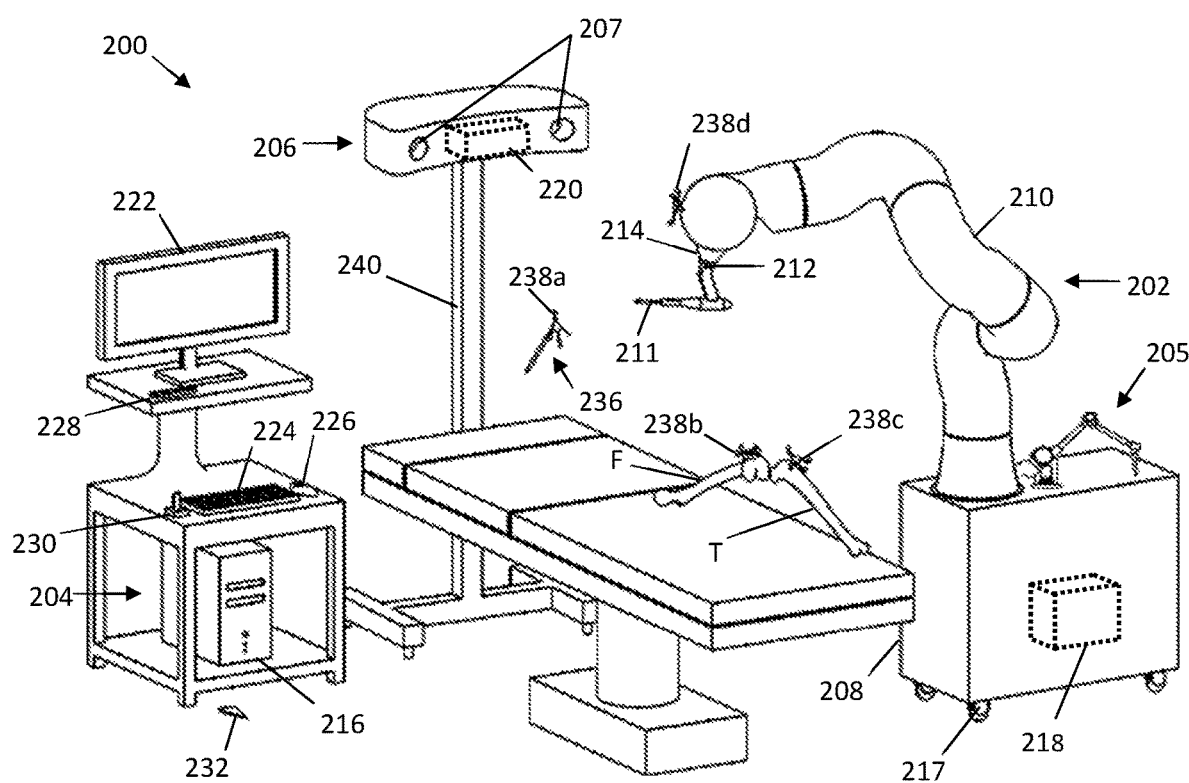
FIG. 6 depicts a robotic surgical system to prepare a bone to receive a robot-specific femoral TKA implant in accordance with embodiments of the invention.

FIG. 6 depicts a robotic surgical system 200 in the context of an operating room (OR) to prepare a bone to receive a robot-specific femoral TKA implant. The surgical system 200 includes a surgical robot 202, a computing system 204, and an optional tracking system 206. The surgical robot 202 may include a movable base 208, a manipulator arm 210 connected to the base 208, an end-effector 211 located at a distal end 212 of the manipulator arm 210, and a force sensor 214 positioned proximal to the end-effector 211 for sensing forces experienced on the end-effector 211. The base 208 includes a set of wheels 217 to maneuver the base 208, which may be fixed into position using a braking mechanism such as a hydraulic brake. The base 208 may further include an actuator to adjust the height of the manipulator arm 210. The manipulator arm 210 includes various joints and links to manipulate the end-effector 211 in various degrees of freedom. The joints are illustratively prismatic, revolute, spherical, or a combination thereof. The end-effector 211 may be motor-driven end-mill, cutter, drill-bit, or other bone removal device.

The computing system 204 may generally include a planning computer 216; a device computer 218; an optional tracking computer 220; and peripheral devices. The planning computer 216, device computer 218, and tracking computer 220 may be separate entities, one-in-the-same, or combinations thereof depending on the surgical system. Further, in some embodiments, a combination of the planning computer 216, the device computer 218, and/or tracking computer 220 are connected via a wired or wireless communication. The peripheral devices allow a user to interface with the surgical system components and may include: one or more user-interfaces, such as a display or monitor 222 to display a graphical user interface (GUI); and user-input mechanisms, such as a keyboard 224, mouse 226, pendent 228, joystick 230, foot pedal 232, or the monitor 222 that in some inventive embodiments has touchscreen capabilities.

The planning computer 216 contains hardware (e.g., processors, controllers, and/or memory), software, data and utilities that are in some inventive embodiments dedicated to the planning of a surgical procedure, either pre-operatively or intra-operatively. This may include reading pre-operative bone data, displaying pre-operative bone data, manipulating pre-operative bone data (e.g., image segmentation), constructing three-dimensional (3D) virtual models, storing computer-aided design (CAD) files, providing various tools, functions, or widgets to aid a user in planning the surgical procedure, and generating surgical plan data. The final surgical plan may include pre-operative bone data, patient data, registration data including the POSE of a set of points defined relative to the pre-operative bone data, trajectory parameters, and/or a set of instructions to operate the surgical robot 202. The set of instructions may include instructions for the surgical robot to modify a volume of bone to receive an implant. The set of instructions may illustratively be: a cut-file having a set of cutting parameters (e.g., cut paths, velocities) to automatically modify the volume of bone; a set of virtual boundaries defined to haptically constrain a tool within the defined boundaries to modify the bone; a set of boundaries coupled with power or actuation control of tracked surgical device to ensure the end-effector only removes bone within the boundaries; a set of planes or drill holes to drill pins or tunnels in the bone; or a graphically displayed navigated set of instructions for modifying the tissue. In particular embodiments, the set of instructions is a cut-file for execution by a surgical robot to automatically modify the volume of bone, which is advantageous from an accuracy and usability perspective. The surgical plan data generated from the planning computer 216 may be transferred to the device computer 218 and/or tracking computer 220 through a wired or wireless connection in the operating room (OR); or transferred via a non-transient data storage medium (e.g., a compact disc (CD), a portable universal serial bus (USB) drive) if the planning computer 216 is located outside the OR.

The device computer 218 in some inventive embodiments is housed in the moveable base 208 and contains hardware, software, data and utilities that are preferably dedicated to the operation of the surgical robotic device 202. This may include surgical device control, robotic manipulator control, the processing of kinematic and inverse kinematic data, the execution of registration algorithms, the execution of calibration routines, the execution of the set of instructions (e.g., cut-files, the trajectory parameters), coordinate transformation processing, providing workflow instructions to a user, and utilizing position and orientation (POSE) data from the tracking system 206. In some embodiments, the surgical system 200 includes a mechanical digitizer arm 205 attached to the base 208. The digitizer arm 205 may have its own tracking computer or may be directly connected with the device computer 218. The mechanical digitizer arm 205 may act as a digitizer probe that is assembled to a distal end of the mechanical digitizer arm 205. In other inventive embodiments, the system includes a hand-held digitizer device 236 with a probe tip.

The optional tracking system 206 may be an optical tracking system that includes two or more optical receivers 207 to detect the position of fiducial markers (e.g., retroreflective spheres, active light emitting diodes (LEDs)) uniquely arranged on rigid bodies. The fiducial markers arranged on a rigid body are collectively referred to as a tracking marker array ($238a$, $238b$, $238c$, $238d$), where each fiducial marker array has a unique arrangement of fiducial markers, or a unique transmitting wavelength/frequency if the markers are active LEDs. An example of an optical tracking system is described in U.S. Pat. No. 6,061,644. The tracking system 206 may be built into a surgical light, located on a boom, a stand 240, or built into the walls or ceilings of the OR. The tracking system computer 220 may include tracking hardware, software, data, and utilities to determine the POSE of objects (e.g., bones B, surgical device 202) in a local or global coordinate frame. The POSE of the objects is collectively referred to herein as POSE data, where this POSE data may be communicated to the device computer 218 through a wired or wireless connection. Alternatively, the device computer 218 may determine the POSE data using the position of the fiducial markers detected from the optical receivers 207 directly.

The POSE data is determined using the position data detected from the optical receivers 207 and operations/processes such as image processing, image filtering, triangulation algorithms, geometric relationship processing, registration algorithms, calibration algorithms, and coordinate transformation processing.

The POSE data is used by the computing system 204 during the procedure to update the POSE and/or coordinate transforms of the bone B, the surgical plan, and the surgical robot 202 as the manipulator arm 210 and/or bone(s) (F, T) move during the procedure, such that the surgical robot 202 can accurately execute the surgical plan.

In another inventive embodiment, the surgical system 200 does not include an optical tracking system, but instead employs a mechanical arm 205 that may mechanically track a digitizer probe assembled to a distal link of the mechanical arm 205. If the bone is not tracked, a bone fixation and monitoring system may fix the bone directly to the surgical robot 202 to monitor bone movement as described in U.S. Pat. No. 5,086,401.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A method to prepare a bone to receive an implant having six or more planar surfaces, comprising:
   planning a position for an implant having six or more planar surfaces relative to pre-operative bone data; and
   preparing the bone with a robotic surgical device to create six or more planar bone cuts complementary to the six or more planar surfaces; and
   creating any remaining planar bone cuts with a manual instrument when the robotic preparation is aborted before the completion of the six or more planar bone cuts.

2. The method of claim 1 wherein the implant is a custom design with a planning software program.

3. The method of claim 2 further comprising manufacturing the implant according to the custom design.

4. The method of claim 1 where the implant is a femoral total knee arthroplasty (TKA) implant.

5. The method of claim 1 wherein the bone is a femur bone.

6. The method of claim 5 further comprising first removing a distal cut plane and creating a pair of peg holes on the femur bone prior to creating any other planar bone cuts.

7. The method of claim 6 wherein the manual instrument is a cut block having a plurality of guide slots to guide a surgical saw to create the remaining planar bone cuts, and a pair of pegs projecting from a bottom surface of the cut block that are placed in the pair of peg holes.

8. The method of claim 1 wherein the manual instrument is a set of cut blocks, wherein each cut block of the set of cut blocks has one or more guide slots at a unique angle and position compared to the other cut blocks of the set of cut blocks.

9. The method of claim 1 wherein the manual instrument comprises a mating surface that is a negative match of a portion of the bone.

10. The method of claim 9 wherein the manual instrument is a three-dimensional (3-D) printed cut guide.

11. The method of claim 1 wherein the manual instrument is a cut block having six or more guide slots.

* * * * *